US010959862B2

(12) United States Patent
Goldfarb et al.

(10) Patent No.: US 10,959,862 B2
(45) Date of Patent: Mar. 30, 2021

(54) PARALLELOGRAM LOAD CELL

(71) Applicant: VANDERBILT UNIVERSITY, Nashville, TN (US)

(72) Inventors: Michael Goldfarb, Franklin, TN (US); Jason Mitchell, Greenbrier, TN (US); Huseyin Atakan Varol, Astana (KZ); Brian Lawson, Nashville, TN (US); Don Truex, Murfreesboro, TN (US)

(73) Assignee: Vanderbilt University, Nashville, TN (US)

(*) Notice: Subject to any disclaimer, the term of this patent is extended or adjusted under 35 U.S.C. 154(b) by 51 days.

(21) Appl. No.: 16/173,519

(22) Filed: Oct. 29, 2018

(65) Prior Publication Data
US 2019/0060091 A1 Feb. 28, 2019

Related U.S. Application Data

(60) Division of application No. 15/180,617, filed on Jun. 13, 2016, now Pat. No. 10,111,762, which is a (Continued)

(51) Int. Cl.
A61F 2/60 (2006.01)
A61F 2/68 (2006.01)
(Continued)

(52) U.S. Cl.
CPC .................. A61F 2/70 (2013.01); A61F 2/60 (2013.01); A61F 2/66 (2013.01); A61F 2/6607 (2013.01);
(Continued)

(58) Field of Classification Search
CPC ..... A61F 2/24; A61F 2/60; A61F 2/68; G01L 1/2243; G01L 1/142; G01L 1/225; G01L 1/226
(Continued)

(56) References Cited

U.S. PATENT DOCUMENTS 6,918,308 B2 7/2005 Biedermann et al.
7,500,407 B2 3/2009 Boiten et al.
(Continued)

FOREIGN PATENT DOCUMENTS

EP 1559384 A1 8/2005
GB 2302949 A 2/1997
KR 20110075151 A 7/2011

OTHER PUBLICATIONS

International Search Report and Written Opinion dated Oct. 30, 2012, in corresponding application No. PCT/US2012/023105.

Primary Examiner — Bruce E Snow
(74) Attorney, Agent, or Firm — Nixon Peabody LLP

(57) ABSTRACT

A device includes a first member and a second member disposed in series along a longitudinal axis. The device also includes links coupling first joints of the first member to second joints of the second member. The first and second members and the links arranged to define a planar parallelogram linkage. The devices also include a resilient element disposed between the first member and the second member, the first member and the second member preloaded against the resilient element. The first member and the second member are preloaded to provide an arrangement of the first and the second joints in which a motion of the first joints with respect to the second joints is constrained to a direction substantially parallel to the longitudinal axis. The devices further include a sensor for generating a signal indicating a separation between the first member and the second member.

15 Claims, 6 Drawing Sheets

Related U.S. Application Data continuation of application No. 14/375,584, filed as application No. PCT/US2012/023105 on Jan. 30, 2012, now abandoned.

(51) Int. Cl.
- *A61F 2/70* (2006.01)
- *G01L 1/22* (2006.01)
- *A61F 2/66* (2006.01)
- *A61F 2/76* (2006.01)
- *G01L 1/14* (2006.01)
- *A61F 2/64* (2006.01)

(52) U.S. Cl.
CPC ............... *A61F 2/76* (2013.01); *G01L 1/142* (2013.01); *G01L 1/2243* (2013.01); *A61F 2/644* (2013.01); *A61F 2002/6614* (2013.01); *A61F 2002/6621* (2013.01); *A61F 2002/6642* (2013.01); *A61F 2002/6664* (2013.01); *A61F 2002/701* (2013.01); *A61F 2002/704* (2013.01); *A61F 2002/762* (2013.01); *A61F 2002/7635* (2013.01)

(58) Field of Classification Search
USPC ...................................................... 623/43, 44
See application file for complete search history.

(56) References Cited

U.S. PATENT DOCUMENTS

| | | |
|---|---|---|
| 2005/0015156 A1 | 1/2005 | Hikichi |
| 2012/0010729 A1 | 1/2012 | Langlois et al. |

PARALLELOGRAM LOAD CELL

CROSS-REFERENCE TO RELATED APPLICATIONS

This application is a division of U.S. Non-Provisional application Ser. No. 15/180,617, entitled "PARALLELOGRAM LOAD CELL" and filed Jun. 13, 2016, which is a continuation of U.S. Non-Provisional application Ser. No. 14/375,584, entitled "PARALLELOGRAM LOAD CELL" and filed Jul. 30, 2014, which is a National Stage Application of International Patent Application No. PCT/US2012/023105, entitled "PARALLELOGRAM LOAD CELL" and filed Jan. 30, 2012. The contents of all of the foregoing are herein incorporated by reference in their entirety as if fully set forth herein.

GOVERNMENT SUPPORT

This invention was made with Government Support under Grant No: EB005684 awarded by the National Institutes of Health (NIH). The Government has certain rights in the invention.

FIELD OF THE INVENTION

The present invention relates to measurement of axial forces, and more specifically to a load cell for measuring an axial force.

BACKGROUND

In many measurement applications, strains or deformations due to bending loads are significantly greater than strains or deformations due to axial loads. Since load cells are generally designed to measure the latter, the presence of bending loads complicates and often compromises the ability to accurately measure axial loads. As a result, even though load cells may be positioned along a longitudinal axis of a member, the resulting load measurement is typically a composite measurement. That is, the bending load may be contributing to the load measurement and introduce significant errors in the load measurement.

These errors can be of particular concern in applications that rely on accurate axial load measurements for control. Such applications can include, among many others, control of lower limb prosthetic, orthotic, or robotic devices. In some control methodologies for lower limb prosthetic, orthotic, or robotic devices, measurements of axial load are often used, alone or in combination with other measurements, to provide device control. However, when bending loads begin to introduce errors into the axial load measurements, the control system may over- or under-compensate in response to such errors. Accordingly, not only may the behavior of such devices no longer approximate natural motion of a lower limb, but may reconfigure the device inappropriately. In the case of prosthetic or orthotic lower limb devices, such inappropriate reconfiguration can result in loss of balance, stumbling, or injury to the user.

In view of such issues, these types of devices are typically fitted with additional sensors in an effort to more accurately determine loads and more precisely control the devices. However, while this addresses the limitations of load cells for such applications, the increase in complexity reduces the robustness of such devices and increases their assembly and maintenance costs.

SUMMARY

Embodiments of the invention concern a load cell device. In the various embodiments devices are provided that include a first member, including first joints, and a second member, including second joints, disposed in series along a longitudinal axis. The devices also include a plurality of links mechanically coupling the first member to the second member via the joints.

The first member, the second member, and the plurality of links are arranged in the various embodiments to define at least one substantially planar parallelogram linkage. The links can be substantially rigid or resilient. In the case of resilient links, the links can be configured to resist substantially any forces not substantially parallel to a plane of the flexible planar parallelogram linkage.

The devices in the various embodiments can also include at least one resilient element disposed between the first member and the second member, where the first member and the second member are preloaded against the resilient element. In the various embodiments, the preloading can be provided via a preload element mechanically coupling the first member and the second member. Exemplary preload elements include spring-loaded shoulder bolts or tension springs. The resilient element in the various embodiments can consist of at least one layer of elastomeric material at least one compression spring.

In the various embodiments, the preloading is configured to provide an arrangement of the joints so that motion of the first joints relative to the second joints is constrained primarily in a direction substantially parallel to the longitudinal axis.

The device further includes at least one sensor for generating at least one signal indicating a separation between the first member and the second member. In at least one configuration, the sensor includes at least one generating element for generating a magnetic field disposed on a first of the first member and the second member and at least one detecting element disposed on a second of the first member and the second member, where the at least one detecting element is configured for detecting magnetic field variation and generating the at least one signal based on the magnetic field variation. Exemplary generating elements include magnets and induction loops.

In an alternative configuration, the sensor is provided using a first capacitive plate on or in the first member, a second capacitive plate on or in the second member, and at least one detecting element coupled to the first and the second capacitive plates and configured for detecting capacitance variation and generating the at least one signal based on the capacitance variation between the plates.

Devices in the various embodiments can also include a controller configured for calculating a current separation between the first member and the second member based on the at least one signal and computing a load along the longitudinal axis based at least on the separation.

One type of device in accordance with the various embodiments is a powered leg device. A powered leg device includes a shank extending substantially along a shank axis and comprising an upper portion with first joints, a lower portion with second joints, a plurality of links mechanically coupling the upper portion to the lower portion via the joints, at least one resilient element disposed between the upper portion and the lower portion, and at least one sensor for generating at least one signal indicating a separation between the upper portion and the lower portion. The powered leg device also includes a foot extending along a foot axis and comprising a resilient toe portion and a resilient heel portion and a powered ankle joint coupling the foot portion to the shank portion. In some configurations, the leg device can also include a powered knee.

In the leg device, the upper portion, the lower portion, and the plurality of links are arranged to define at least one planar parallelogram linkage having a plane of motion substantially parallel to the foot axis, and wherein the first member and the second member are preloaded against the resilient element. The preloading is configured to provide an arrangement of the joints so that motion of the first joints relative to the second joints is constrained primarily in a direction substantially parallel to the shank axis.

The leg device also includes a controller for operating the leg device. In some embodiments the controller can be configured for determining the load on each of the resilient toe portion and the resilient heel portion based on the at least one signal.

The various embodiments also include methods and computer readable mediums for operating the devices in accordance with the various embodiments.

DETAILED DESCRIPTION

Figure 1A:
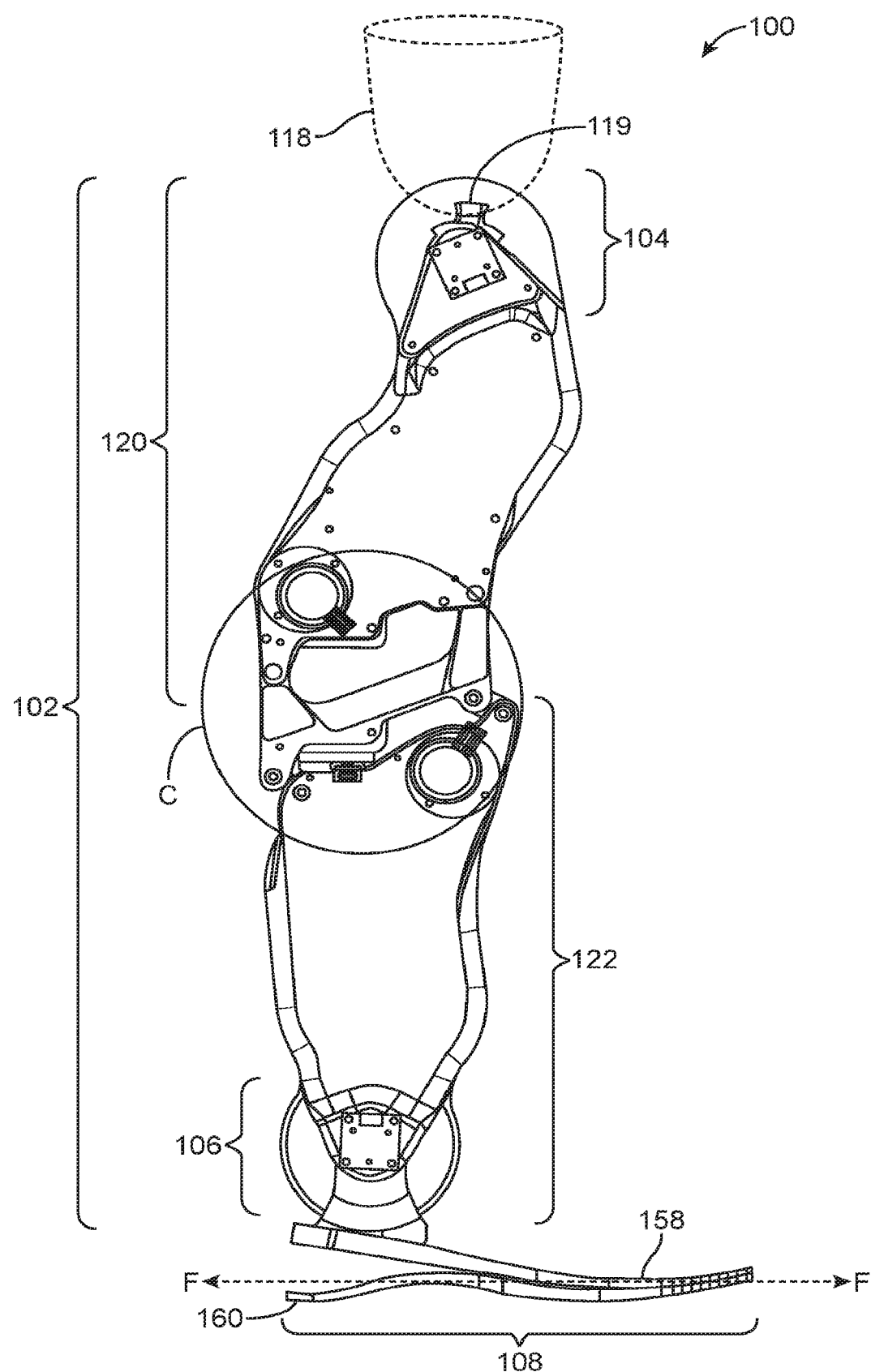
FIG. 1A is lateral view of a leg device according to an embodiment.
Figure 1B:
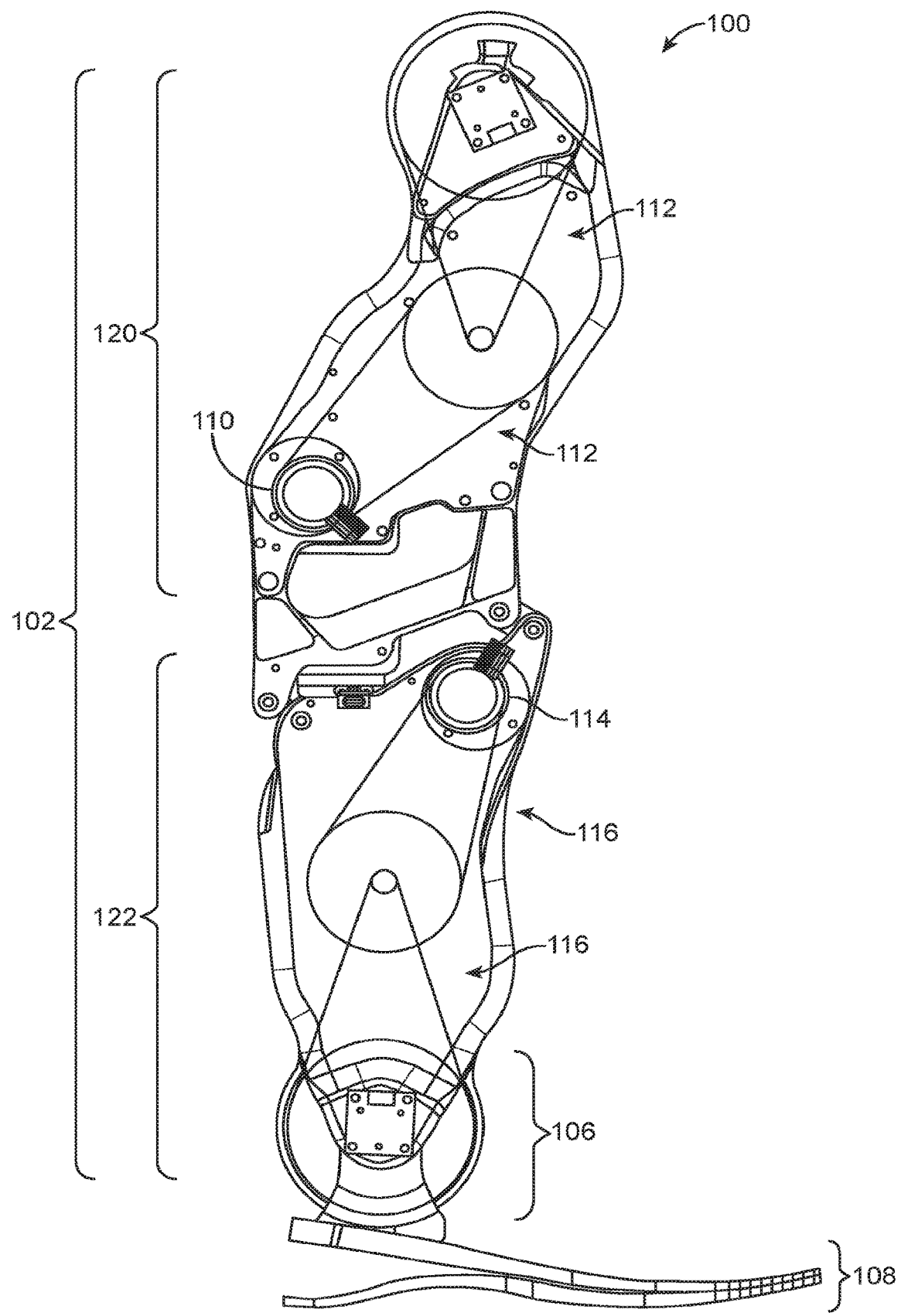
FIG. 1B is a cutaway view of the leg device of FIG. 1A.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, one challenge in control of prosthetics, orthotics, or robotics is obtaining an accurate measurement of an axial load along a lower limb device, such as a leg device. Existing methodologies generally rely on a complicated system of sensors measuring the various forces and loads encountered by such a device. In view of the limitations of such existing systems, the various embodiments of the invention provide a new load cell for measuring axial loads and devices including such load cells.

In particular, the various embodiments provide a load cell that measures axial forces in the presence of moments by relating the loads to displacements through a compliant medium, and isolating the displacement due to the axial force with a substantially planar parallelogram linkage. Accordingly, the load cell is capable of providing a measurement of axial force that includes little or no components related to bending loads experienced by the device.

A prosthetic leg device 100 including a load cell in accordance with the various embodiments is illustrated in FIGS. 1A-1E. Although the various embodiments will be generally described with respect to a prosthetic leg device, the invention is not limited in this regard. The various embodiments are equally applicable to any application in which it is desirable to obtain a measure of axial load substantially unaffected by bending loads. These can include applications in prosthetics, orthotics, and robotics, to name a few.

The leg device 100 in FIGS. 1A-1E includes a shank 102 extending substantially along a shank axis S, with a powered knee joint 104, a powered ankle joint 106, and a flexible foot 108 extending along a foot axis F. The powered knee joint 104 can be articulated using a knee motor 110 and one or more knee drive stages 112. The powered ankle joint 106 can be articulated using a ankle motor 114 and one or more ankle drive stages 116. A socket 118 can be coupled to a socket interface 119 of the powered knee joint 104 and can be used to attach the leg device 100 to a user. However, the various embodiments are not limited to devices utilizing a socket arrangement. Rather, any other attachment means can be used in the various embodiments without limitation.

Although a particular configuration for leg device 100 is illustrated in FIG. 1A-1E, the various embodiments are not limited in this regard and other configurations can be used. For example, some alternate configurations for leg device are described in U.S. patent application Ser. No. 12/427,384 to Goldfarb et al., filed Apr. 29, 2009 and entitled "POWERED LEG PROSTHESIS AND CONTROL METHODOLOGIES FOR OBTAINING NEAR NORMAL GAIT", the contents of which are herein incorporated by reference in their entirety.

Further, although the leg device 100 is configured for an above-the-knee amputee, this is solely for ease of illustration and the various embodiments are not limited in this regard. That is, the leg device 100 can be alternatively configured for below-knee amputees. Further, as noted above, the various embodiments are equally useful for devices beyond prosthetic, orthotic, and robotic devices.

The leg device 100 can also include a power supply (not shown), plurality of sensors (not shown), and a control system (not shown) for operating the leg device 100. Such sensors can include load sensors, joint torque sensors, joint position sensors, sagittal moment sensors, accelerometers, current sensors, and voltage sensors, to name a few. These sensors can be used with the controller to generate signals for adjusting the torque and positions of the powered knee joint 104 and the powered ankle joint 106. Various types of control systems can be used in the various embodiments of the invention. For example, one control system that can be used is that described in U.S. patent application Ser. No. 12/427,384, filed Apr. 29, 2009 and entitled "POWERED LEG PROSTHESIS AND CONTROL METHODOLOGIES FOR OBTAINING NEAR NORMAL GAIT", the contents of which are herein incorporated by reference in their entirety. Another control system that can be used is that described in PCT Application No. PCT/US11/53501, filed Sep. 27, 2011 and entitled "MOVEMENT ASSISTANCE DEVICE", the contents of which are herein incorporated by reference in their entirety. Still another control system that can be used is that described in PCT Application No. PCT/US10/54655, filed Oct. 29, 2010 and entitled "SYSTEMS AND CONTROL METHODOLOGIES FOR IMPROVING STABILITY IN POWERED LOWER LIMB DEVICES", the contents of which are herein incorporated by reference in their entirety.

The control system and power supply can be integrated into the leg device 100. However, the various embodiments are not limited in this regard and can be used with leg devices having an external control system, an external power supply, or both. However, the various embodiments are not limited to the control systems described above. Rather, any other leg device control systems can be used in the various embodiments.

As described above, among the various sensors within leg device 100 are load sensors. At least one of these load sensors can be a load cell configured in accordance with the various embodiments. A load cell in accordance with the various embodiments is provided in the various embodiments by introducing a parallelogram linkage along the length of shank 102. In particular, the shank 102 is divided into a first member or upper portion 120 and a second member or lower portion 122. The upper portion 120 is configured to have at least first and second upper joints or link points 124, 126 and the lower portion 122 is configured to have at least first and second lower joints or link points 128, 130. A first link 132 can be used to mechanically couple joints 124 and 128 using first link pins 134 while a second link 136 can be used to couple joints 126 and 130 using second link pins 138. The joints 124, 126, 128, 130, the links 132, 136, and the pins 134, 138 are arranged to form a planar parallelogram linkage. As used herein, the term "planar parallelogram linkage" refers to a four bar linkage in which opposite bars are of equal length and such that motion is constrained substantially to a single plane. As used herein, the term "substantially" refers to being within 20% of the stated value or condition.

Figure 1C:
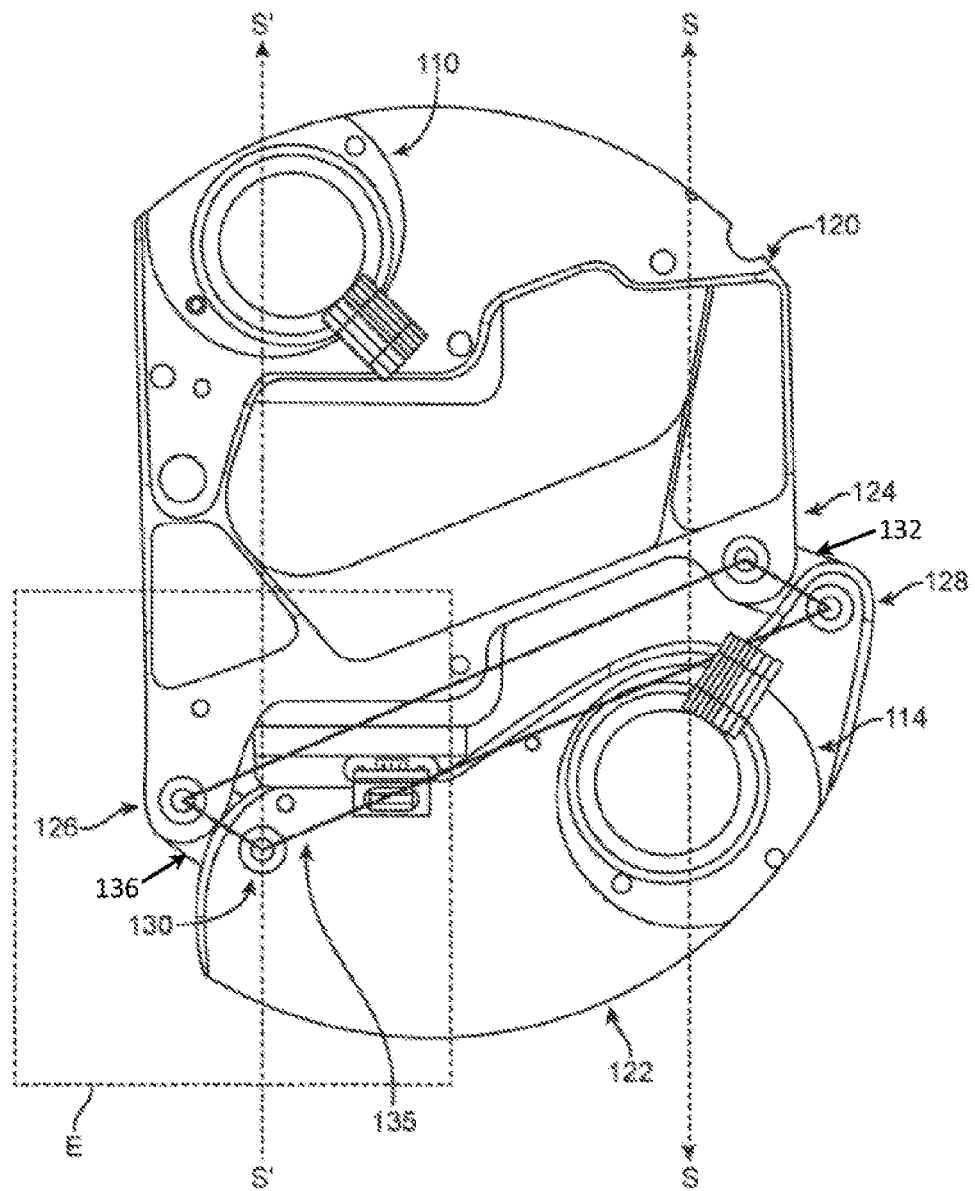
FIG. 1C is a detailed view of area C in FIG. 1A.

Accordingly, in leg device 100, the links 134 and 136 form a first set of opposite bars of the linkage and the upper portion 120 and the lower portion 122 form the second set of opposite bars of the linkage. Together, these define a parallelogram 135 with vertices defined by joints 124, 126, 128, and 130, as illustrated in FIG. 1C. In leg device 100, parallelogram 135 has non-equal sides with longer sides intersecting shank axis S or another axis parallel to shank axis S. However, the various embodiments are not limited in this regard and the sides of parallelogram 135 can be substantially equal.

In addition to the planar parallelogram linkage, the load cell also includes a displacement sensor 140 disposed between the upper portion 120 and the lower portion 122. The displacement sensor 140 can include a sensor resilient element 142 disposed between a sensor top element 144 and a sensor bottom element 146, where the sensor elements 142, 144, and 146 are arranged in series along an axis substantially parallel to the shank axis S.

In the various embodiments, the sensor resilient element 142 is an element configured to compress or deform in response to a force applied by the sensor top element 144 and the sensor bottom element 146 against the sensor resilient element 142. The sensor resilient element 142 is also configured to apply a restorative force against the sensor top element 144 and the sensor bottom element 146 in response to this applied force.

The sensor resilient element 142 can be formed in a variety of ways. For example, in some embodiments, the sensor resilient element 142 can be an elastomer or any other type of natural or synthetic viscoelastic material. In other embodiments, the sensor resilient element 142 can be a spring or resilient mechanical device. For example, in some embodiments, the sensor resilient element 142 can be a compression spring, including, but not limited to coil springs, leaf springs, spring washers and the like. However, the various embodiments are not limited in this regard and other equivalents to a compression spring can be used in the various embodiments without limitation.

In contrast to the sensor resilient element 142, the sensor top element 144 and the sensor bottom element 146 can be formed from materials that are substantially non-viscoelastic or having viscoelastic properties that are significantly less pronounced than those of the sensor resilient element 142. In other words, the sensor resilient element 142, the sensor top element 144, and the sensor bottom element 146 are configured such that when forces are applied along the shank axis S, deformation will occur primarily and more notably in the sensor resilient element 142, with the sensor top element 144 and the sensor bottom element 146 remaining relatively undeformed.

Further, sensor resilient element 142, the sensor top element 144 and the sensor bottom element 146 can be arranged so that a force applied to sensor resilient element 142 by the sensor top element 144 and the sensor bottom element 146 is substantially parallel to shank axis S. For example, as shown in FIGS. 1A-1E, the sensor top element 144 and the sensor bottom element 146 are configured to mate or be attached to other portions of leg device 100 so that surfaces facing the sensor resilient element 142 are substantially perpendicular to the shank axis S.

Figure 1D:
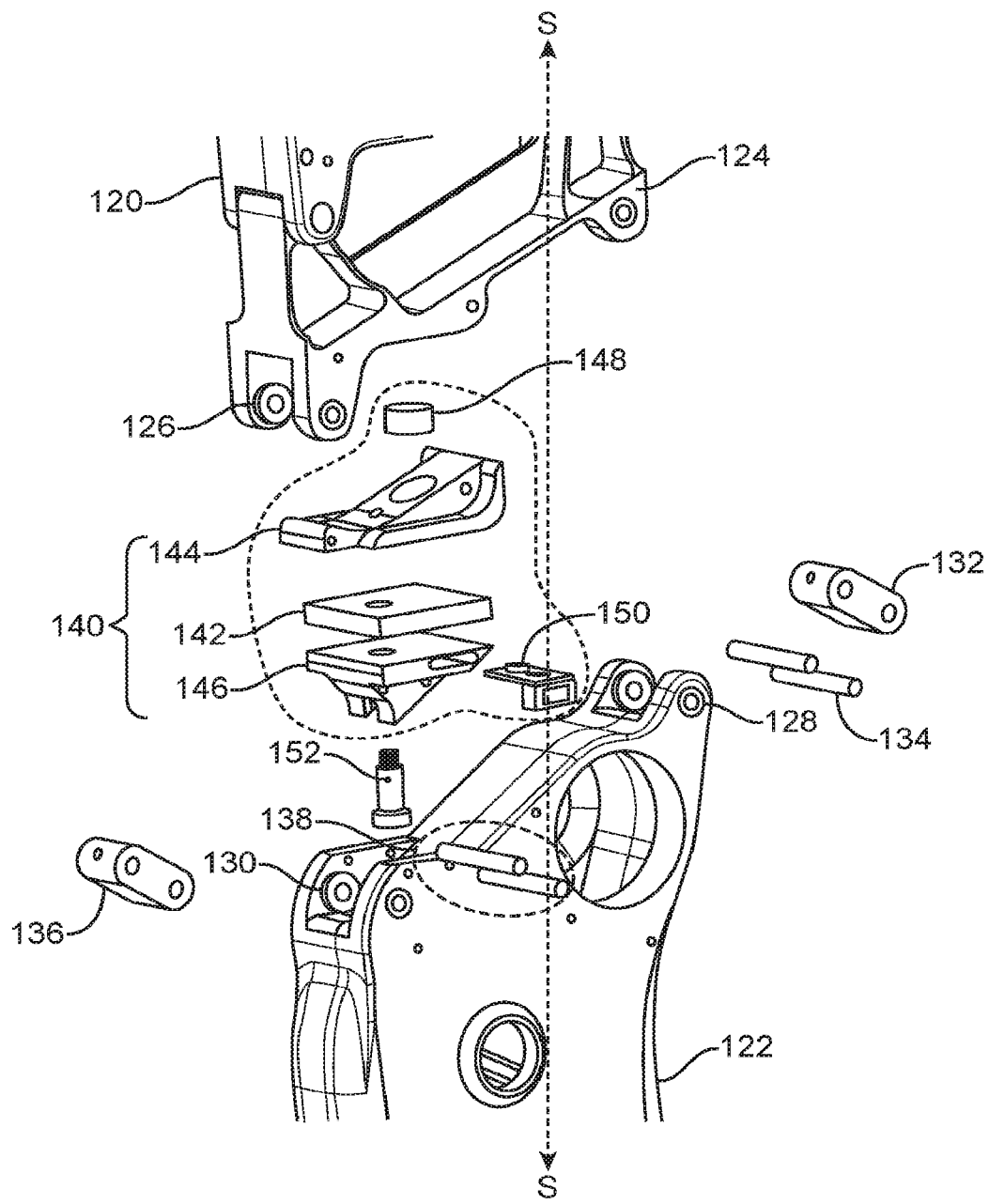
FIG. 1D is an exploded view of area C in FIG. 1A.

In addition to elements 142, 144, and 146, the displacement sensor 140 also includes a means for generating a signal indicating the amount of deformation of sensor resilient element 142, or alternatively, a change in the spacing between the sensor top element 144 and the sensor bottom element 146. In the exemplary embodiment of FIGS. 1A-1E, this is provided via a permanent magnet 148 and a magnetic field sensor 150. In particular, the permanent magnet 148 can be disposed in one of the sensor top element 144 and the sensor bottom element 146 and the magnetic field sensor 150 can be disposed in the other. As shown in FIG. 1D, the exemplary configuration shows the permanent magnet 148 disposed in sensor top element 144 and the magnetic field sensor 150 disposed in the sensor bottom element 146. In operation, as the sensor resilient element 142 is deformed in response to a force applied by the sensor top element 144 and the sensor bottom element 146, the distance between the permanent magnet 148 and the magnetic field sensor 150 will decrease. As a result, the magnetic field experienced by the magnetic field sensor 150 will increase. As the sensor resilient element 142 restores in response to a reduction in the force applied by the sensor top element 144 and the sensor bottom element 146, the distance between the permanent magnet 148 and the magnetic field sensor 150 will increase. As a result, the magnetic field experienced by the magnetic field sensor 150 will increase. Accordingly, based on the configuration of the elements of the displacement sensor 140, the amount of deformation of sensor resilient element 142 in a direction along shank axis S can be estimated with a high degree of accuracy based on the changes in the magnetic field.

In the various embodiments, other methods can also be used to determine the amount of deformation of sensor resilient element 142 in a direction along shank axis S. For example, in some embodiments, an induction loop (not shown) can be used in place of the permanent magnet 148 to generate the magnetic field detected by magnetic field sensor 150.

In other embodiments, a pair of capacitive plates can be used instead or in addition to permanent magnet 148 and magnetic field sensor 150. For example, the sensor top element 144 and the sensor bottom element 146 can be configured as or can include first and second capacitor plates with facing surfaces that are substantially perpendicular to the shank axis S. A detecting element (not shown) can then be coupled to the first and the second capacitive plates and configured for detecting capacitance variations, which correspond to changes in the distance between the sensor top element 144 and the sensor bottom element 146, and thus changes in the deformation of sensor resilient element 142 in a direction along shank axis S. The detecting element can be incorporated into the control system for leg device 100 or can operate independently. Any methods for measuring capacitance can be used in the various embodiments without limitation.

Any other methods for detection of the distance between the sensor top element 144 and the sensor bottom element 146, and thus deformation of sensor resilient element 142 can also be used in the various embodiments without limitation.

In addition to the foregoing elements, the leg device 100 can also include a biasing or preload element 152. The preload element 152 is configured to bias or preload the upper portion 120 against the lower portion 122, such that these portions maintain contact with the resilient element 142, even in the presence of a tensile load.

For example, in some embodiments, the parallelogram linkage defined by links 132, 136, pins 134, 138, and joints 124, 126, 128, 130 can be preloaded to define a parallelogram with unequal angles. In particular, a configuration that reduces the distance or spacing between the long sides of the parallelogram 135, such as the configuration in FIG. 1C. This preloading of the upper portion 120 against the lower portion 122 thus results in the parallelogram 135 always being maintained as a parallelogram with unequal angles, whether or not a force is applied along shank axis S.

In the various embodiments, the preload element 152 can be provided in various ways. In one configuration, as illustrated in FIG. 1D, the preload element 152 can be a spring-loaded shoulder bolt. In another configuration, the preload element can be one or more tension springs connecting upper member 120 to lower member 122. However, the various embodiments are not limited to these configurations. Rather, any means of applying tension or force between upper member 120 and lower member 122 can be used in the various embodiments.

In the various embodiments, the configuration and locations of links 132, 136, pins 134, 138, and joints 124, 126, 128, 130, the amount of preloading, and the configuration of the displacement sensor 140, is selected such that a force applied along shank axis S results in motion of joints 124, 126, 128, 130 that is primarily in a direction parallel to shank axis S. This is illustrated in further detail with respect to FIGS. 1D and 1E.

Figure 1E:
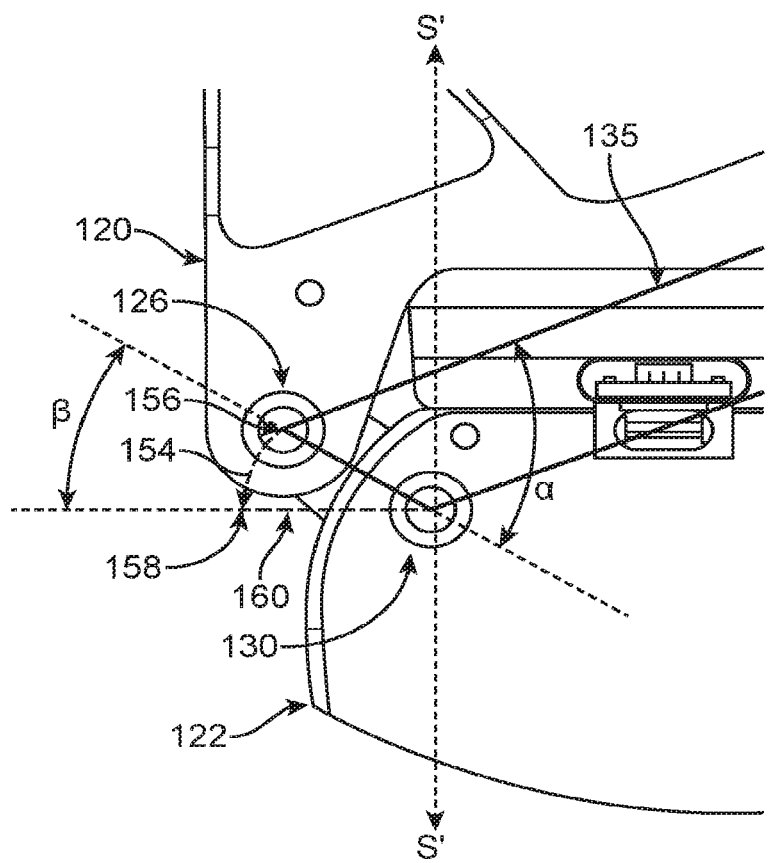
FIG. 1E is a detailed view of area E in FIG. 1C.

Referring to FIGS. 1C, 1D, and 1E, one will note that arranging the parallelogram linkage in certain configurations can be advantageous. First, in order to nominally align the movement of the upper and lower portions of the load cell with the applied axial load, the links 132 and 136 can be arranged to be substantially perpendicular to the shank axis S after pre-loading. Second, to minimize the total height of the load cell (i.e., length along the shank axis S) the distance between the members should be reduced as much as possible. Third, as each joint in the linkage will typically contain some degree of backlash, the effect of such backlash on the movement of the upper and lower portions of the parallelogram load cell can be minimized by increasing the distance between pivot points 124 and 126 and the distance between pivot points 128 and 130.

In order to balance these three objectives, the configuration shown in FIG. 1E, with nominal linkage angle α and orientation angle β is proposed. As the linkage angle α becomes small, the linkage approaches a kinematic singularity (i.e., all links are nearly aligned) at which the linkage fails to operate effectively, particularly in the presence of backlash in the joints. Therefore, the geometry of the linkage can be selected to balance the objectives of 1) low total height, 2) large distance between links, 3) nominal configuration of links perpendicular to shank axis S (i.e., select β to be small), and 4) avoiding linkage singularity (i.e., select α to be large). If the measurement technique used to measure the distance between the upper and lower portions of the load cell is relatively insensitive to lateral movement, an effective balance between these objectives can be achieved by allowing some lateral motion (i.e., beta greater than zero), which allows an increase in the angle alpha, and thus enhances the linkage performance. For example, an effective configuration is illustrated in FIGS. 1C and 1E, where the linkage angle α is approximately 45 degrees (i.e., the linkage is far from a singularity), and the motion angle β is approximately 30 deg (the lateral movement is still small relative to the axial movement). Further, in this configuration, the distance between pivot points is large (relative to geometric constraints), and the total length along the S-axis is small (relative to sensing element).

As a result of this configuration, when a force is applied along shank axis S, joint 126 will travel along an circular arc 154 (constrained to motion angle β) about joint 130 from a first position 156 to as far as a second position 158. Similarly, the joint 124 would travel in a circular arc with respect to joint 128. The present inventors have recognized that if the circular arc 154 is constrained to a particular set of angles with respect to an axis S' through joint 130 and that is substantially parallel to shank axis S, the motion along circular arc 154 will consist primarily of motion parallel to shank axis S. For example, if the range of motion for circular arc 154 is constrained to less than or equal to 30 degrees (i.e., constrained to motion angle β, the motion perpendicular to shank axis S will be less than the motion parallel to shank axis S. As a result, using such a configuration, any subsequent motion can be assumed to correspond to the amount of deformation in displacement sensor 140 parallel to shank axis S'.

Further, it is noted that in this configuration, the joints 124, 126, 128, 130 are arranged with joints 124 and 128 closer to the anterior of leg device 100 and with joints 126 and 130 closer to the posterior of leg device 100. Assuming the pivot points contain some non-zero amount of friction, this configuration (shown in FIG. 1A) will slightly favor measurement of ground reaction forces with an anterior bias, since in this case the total force generally more perpendicular to the links 132 and 136. Mirroring the linkage geometry would slightly enhance sensitivity to ground reaction forces with a posterior bias.

In view of the foregoing, the displacement sensor 140 can then be used to provide a good estimate of force along shank axis S. First, the use of a substantially planar parallelogram linkage substantially constrains motion to a plane of parallelogram 135. Therefore, even if substantial bending loads are provided perpendicular to the plane of parallelogram 135, these are not experienced by displacement sensor 140. Second, the configuration and locations of links 132, 136, pins 134, 138, and joints 124, 126, 128, 130, and the amount of preloading, constrains motion parallel to parallelogram 135 to a limited range of motions composed primarily of motions parallel to the shank axis S. Therefore, even if substantial bending loads are provided parallel to the plane of parallelogram 135, the parallelogram linkage will not respond significantly to these bending loads. Therefore, these bending loads will therefore not significantly contribute, if at all, to the signals from displacement sensor 140. Accordingly, since the displacement sensor 140 is providing a signal that reflects substantially the displacement parallel to shank axis S, the force along shank axis S can then be directly estimated from the signal from displacement sensor 140.

In the various embodiments, the calculation of the force along shank axis S can be performed within the control system of leg device 100 or in a separate element which provides the force value to the control system for use therein. In some embodiments, the force value can be calculated each and every time based on the detected magnetic field and the deformation characteristics of the sensor resilient element 142. In other embodiments, a lookup table of forces as a function of the detected signal (e.g., magnetic field, capacitance) can be stored in the control system. A lookup operation can then be performed to obtain the correct force value. In some cases, the lookup operation can include performing an interpolation step to obtain the correct force value.

The various embodiments are not limited solely to estimating force along the shank axis S. In some embodiments, the estimate of force along the shank axis S can be combined with knowledge of torque at ankle joint 106 (e.g., from torque sensors) to estimate loads at a toe 158 and a heel 160 loads in flexible foot prosthesis 108. Accordingly, separate sensors for determining loads at the toe 158 and heel 160 can be eliminated, reducing complexity of the leg device 100 and associated costs.

To estimate loads at the toe 158 and heel 160 in the various embodiments, the assumption can be made that a surface on which leg device 100 operates (e.g., the ground) imposes forces on the flexible foot 108 in two principal locations. These locations are at the heel 160 and the toe 158 (or ball of foot). Using this assumption, and having knowledge of the resilient characteristics of the flexible foot 108 and the distance along the foot axis F from the ankle joint 106 to the heel 160 and the ankle joint 106 to the toe 158, respectively, the sum of the loads at heel 160 and toe 158 must be approximately equal to the force along shank axis S of the leg device 100. Further, assuming the force value obtained based on displacement sensor 140 passes through the ankle joint 106, the difference between the loads at the toe 158 and heel 160 loads (weighted by their respective distances from the ankle) are equal to the known torque for the ankle joint 106. In other words, the force at toe 158 can be estimated as:

$$F_{toe} = \frac{F_{shank} * d_{heel} + \tau_{ankle}}{d_{toe} - d_{heel}} \quad (1)$$

and $$F_{heel} = \frac{F_{shank} * (d_{toe} - d_{heel}) - \tau_{ankle}}{d_{toe} - d_{heel}}, \quad (2)$$

where $F_{shank}$ is the force along shank axis S, $d_{toe}$ is the distance between toe 158 and ankle joint 106 along foot axis F at equilibrium, $d_{heel}$ is the distance between heel 160 and ankle joint 106 along foot axis F at equilibrium, and $\tau_{ankle}$ is the torque at ankle joint 106.

In view of the foregoing, a control system can be provided for robotic, prosthetic, or orthotic devices which can control operation of a leg device with a substantially smaller number of sensors. In particular, as noted above, the various embodiments allow the parallelogram load sensor to provide at least three measurements of forces (or estimates thereof) from a single measurement of displacement. Knowledge of heel and/or ball of foot load provides important information for device control (i.e., the control system needs to detect the difference between the heel strike and toe-off events during walking). The capability to detect heel and ball of foot loads without sensors on the foot eliminates the need for wires crossing the ankle joint, and generally results in a more robust device. This reduces overall device complexity and costs.

Although the various embodiments have been described generally with respect to a parallelogram linkage formed via links physically and mechanically connecting an upper member to a lower member, the invention is not limited in this regard. In some embodiments, rather than providing links for physically and mechanically connecting the upper portion to the lower portion, the parallelogram linkage can be formed separately and the linkage itself can be utilized to attach the upper portion to the lower portion. Such a linkage is illustrated in FIGS. 2A and 2B.

Figure 2A:
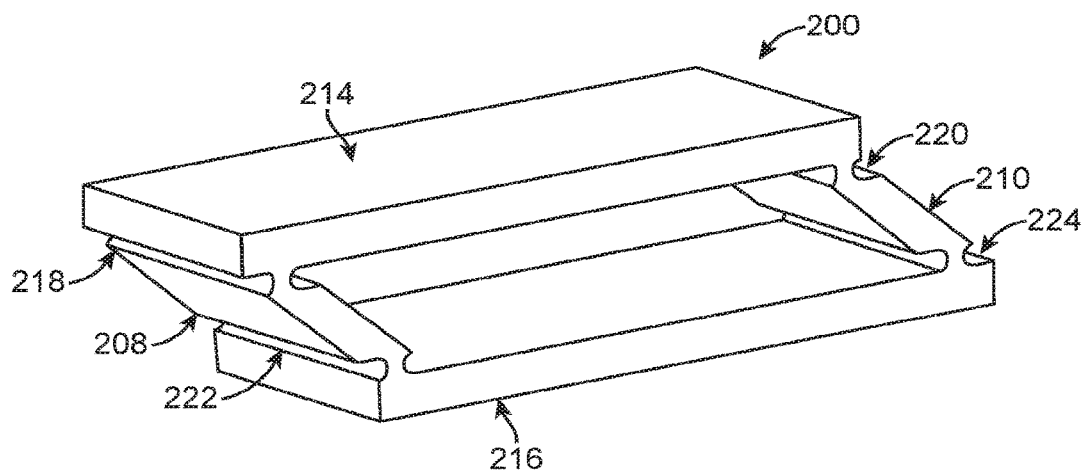
FIG. 2A is a first view of a parallelogram linkage according to an alternate embodiment.
Figure 2B:
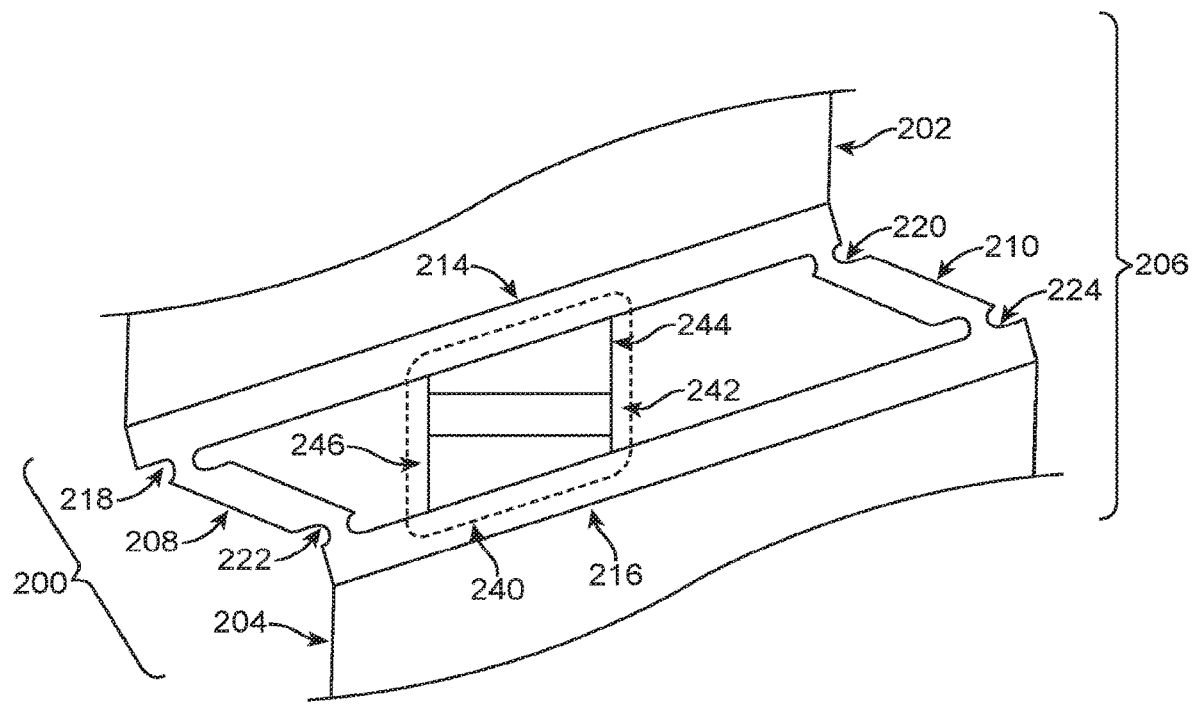
FIG. 2B is a partial view of a leg device including the linkage of FIG. 2A.

As shown in FIGS. 2A and 2B, a parallelogram linkage 200 can be provided for insertion between an upper portion 202 and a lower portion 204 of a shank 206, where the parallelogram linkage 200 is utilized in substantially the same way as the linkage described above with respect to FIGS. 1A-1E. Similar to the configuration in FIGS. 1A-1E, the parallelogram linkage 200 can include a first set of opposite links 208 and 210 that can be used to define a first set of bars 210 of the parallelogram linkage 200. However, rather than utilizing the upper portion 202 and the lower portion 204 of the shank 206 to form the second set of bars 212 of the parallelogram linkage 200, a discrete upper link 214 and a discrete lower link 216 can be provided to form the second set of bars 212 for the parallelogram linkage 200. In such a configuration, discrete links 214 and 216 can also be used to mechanically couple the parallelogram linkage 200 to the upper portion 202 and the lower portion 204.

In some embodiments, the links 208, 210, 214, and 216 can be physically and mechanically connected via a set of discrete joints 218, 220, 222, and 224 and configured and operated substantially in the same manner as described above with respect to FIGS. 1A-1E. For example, the links 208, 210, 214, 216 and the joint 218, 220, 222, 224 can be substantially non-resilient elements. Further a sensor 240 can measure the relative distance between upper portion 202 and lower portion 204 of shank. Optionally, the sensor 240 can include, as in FIGS. 1A-1E, a resilient element 242, a second top element 244, and a sensor bottom element 246. However, in many embodiments the resilient member 242 is not necessary, as the linkage 200 effectively operates as the deformable element.

In the embodiments described above, the links 208, 210, 214, 216 and the joints 218, 220, 222, 224 are generally described as discrete separate elements. However, in some embodiments, as illustrated in FIGS. 2A and 2B, these can be integrally formed. That is, as illustrated in FIGS. 2A and 2B, the parallelogram linkage 200 can be formed as a single parallelogram element that defines the links 208, 210, 214, 216 and such that the portions of the single element define joints. For example, as shown in FIGS. 2A and 2B, the union between links links 208, 210, 214, 216 can be defined by cutouts at joints 218, 220, 222, 224. Thus, when a force is applied to parallelogram linkage 200, the parallelogram linkage 200 will preferentially deform at joints 218, 220, 222, 224. Alternatively, the parallelogram linkage 200 can be arranged such that the parallelogram linkage 200 will preferentially deform at joints 218, 220, 222, 224 without such cutouts or features. For example, by configuring the parallelogram linkage 200 to have a shape at equilibrium that is substantially non-rectangular, such that an applied force results in deformation primarily in a direction parallel to shank axis, as described above, and by constructing the parallelogram linkage 200 from substantially resilient materials.

An advantage of using a single parallelogram element is that the need for pre-loading of the parallelogram linkage 200 can be eliminated since the parallelogram linkage 200 can be pre-configured in the pre-loaded state. That is, in a substantially non-rectangular state such that an applied force results in deformation primarily in a direction parallel to shank axis. Additionally, in some embodiments, the resilient element can be eliminated as the parallelogram linkage 200 can also operate as the resilient element.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A device, comprising:
    a first member and a second member disposed in series along a shank axis, the first member comprising first joints and the second member comprising second joints;
    a first link mechanically coupling the first member to the second member via one of the first joints and one of the second joints, and a second link mechanically coupling the first member to the second member via another of the first joints and another of the second joints;
    at least one sensor for generating at least one signal indicating a separation between the first member and the second member; and
    the first member, the second member, and the first and second links are arranged to define at least one substantially planar parallelogram linkage when disposed in both a first position and a second position,
    the at least one substantially planar parallelogram linkage having a range of motion constrained between the first position and second position,
    wherein when the at least one substantially planar parallelogram linkage moves from the first position to the second position, the distance traveled by one of the first joints relative to one of the second joints is greater in a direction parallel to the shank axis than in a direction perpendicular to the shank axis.

2. The device of claim 1, further comprising:
    a pre-load element for biasing the first member towards the second member; and
    a resilient element for biasing the first member away from the second member.

3. The powered leg device of claim 2, wherein the preload element comprises at least one spring-loaded shoulder bolt.

4. The powered leg device of claim 2, wherein the preload element comprises at least one tension spring.

5. The powered leg device of claim 2, wherein the resilient member is disposed between the first member and the second member.

6. The device of claim 2, wherein the at least one resilient element comprises at least one layer of elastomeric material.

7. The device of claim 2, wherein the at least one resilient element comprises at least one compression spring.

8. The device of claim 1, wherein the first and second links comprise first and second substantially rigid links.

9. The device of claim 1, wherein the first and second links comprise first and second resilient links, each of the first and second resilient links configured to resist substantially any force not substantially parallel to a plane of the planar parallelogram linkage.

10. The device of claim 1, wherein the at least one sensor comprises:
    at least one generating element disposed on a first of the first member and the second member and configured for generating a magnetic field; and
    at least one detecting element disposed on a second of the first member and the second member and configured for generating the at least one signal based on a magnetic field variation.

11. The device of claim 10, wherein the at least one generating element is a magnet.

12. The device of claim 10, wherein the at least one generating element is an induction loop.

13. The device of claim 1, wherein the at least one sensor comprises:
   a first capacitive plate on or in the first member;
   a second capacitive plate one or in the second member; and
   at least one detecting element coupled to the first and the second capacitive plates and
   configured for detecting capacitance variation and generating the at least one signal based on the capacitance variation.

14. The device of claim 1, further comprising a controller, wherein the controller is configured for:
   computing a load along the shank axis based at least on the signal indicating a separation between the first member and the second member.

15. The device of claim 1, wherein the first and second links are coupled to the first member and the second member using a plurality of torsion springs.

\* \* \* \* \*